(12) United States Patent
Beier et al.

(10) Patent No.: US 8,940,899 B2
(45) Date of Patent: Jan. 27, 2015

(54) PROCESS FOR THE PREPARATION OF 5-SUBSTITUTED 1-ALKYLTETRAZOLYL OXIME DERIVATIVES

(75) Inventors: Christian Beier, Bergisch Gladbach (DE); David Bernier, Lyons (FR); Pierre-Yves Coqueron, Lyons (FR); Philippe Desbordes, Lyons (FR); Christophe Dubost, Charbonnieres-les-Bains (FR); Norbert Lui, Odenthal (DE); Sergii Pazenok, Solingen (DE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 13/807,101

(22) PCT Filed: Jun. 27, 2011

(86) PCT No.: PCT/EP2011/060675
§ 371 (c)(1),
(2), (4) Date: Dec. 27, 2012

(87) PCT Pub. No.: WO2012/000918
PCT Pub. Date: Jan. 5, 2012

(65) Prior Publication Data
US 2013/0102786 A1 Apr. 25, 2013

Related U.S. Application Data

(60) Provisional application No. 61/359,064, filed on Jun. 28, 2010.

(30) Foreign Application Priority Data

Jun. 28, 2010 (EP) .................................... 10167449

(51) Int. Cl.
| | | |
|---|---|---|
| *C07D 277/00* | (2006.01) | |
| *A01N 43/40* | (2006.01) | |
| *C07D 401/00* | (2006.01) | |
| *C07D 419/00* | (2006.01) | |
| *C07D 401/12* | (2006.01) | |
| *C07D 417/12* | (2006.01) | |

(52) U.S. Cl.
CPC ............ *C07D 401/12* (2013.01); *C07D 417/12* (2013.01)
USPC ......................... 546/268.4; 514/340; 548/197

(58) Field of Classification Search
CPC .. C07D 401/12; C07D 401/04; C07D 401/14; C07D 257/04; C07D 409/14; C07D 277/52; C07D 277/48; C07D 277/18; C07D 277/28; C07D 417/06; A61K 31/427
See application file for complete search history.

(56) References Cited

U.S. PATENT DOCUMENTS

2002/0193398 A1* 12/2002 Barrow et al. ................. 514/300
2005/0070439 A1* 3/2005 Kobori et al. .................. 504/261

FOREIGN PATENT DOCUMENTS

WO WO 2011/161076 12/2011

OTHER PUBLICATIONS

Yates, P. et al. Aliphatic Diazo Compounds. VIII. The Reaction of Diazo Ketones with Bases. II. Journal of the American Chemical Society. 1963, vol. 85, No. 19, p. 2970.*
U.S. Appl. No. 13/805,276 corresponding to PCT/EP2011/060281, having an International filing date of Jun. 21, 2011, published as WO 2011/161076 by Christian Beier et al.
International Search Report mailed Jul. 29, 2011 in corresponding International Application No. PCT/EP2011/060675.
Peter Yates, et al.: "Aliphatic Diazo Compounds. VIII. The Reaction of Diazo Ketones with Bases, II", Journal of the American Chemical Society, American Chemical Society, vol. 85, No. 19, Oct. 5, 1963, pp. 2967-2976, XP002580503, ISSN: 0002-7863.

\* cited by examiner

*Primary Examiner* — Janet L Andres
*Assistant Examiner* — Ben S Michelson
(74) *Attorney, Agent, or Firm* — Ostrolenk Faber LLP

(57) ABSTRACT

The present invention relates to a process for the preparation of 5-substituted 1-alkyltetrazolyl oxime derivatives.

7 Claims, No Drawings

PROCESS FOR THE PREPARATION OF 5-SUBSTITUTED 1-ALKYLTETRAZOLYL OXIME DERIVATIVES

CROSS-REFERENCE TO RELATED APPLICATION(S)

The present application is a 35 U.S.C. §371 national phase conversion of PCT/EP2011/060675, filed on Jun. 27, 2011, which claims priority of European Application No. 10167449.7, filed on Jun. 28, 2010, and of U.S. Provisional Application No. 61/359,064, filed on Jun. 28, 2010. Applicants claim priority to each of the foregoing patent applications. The PCT International Application was published in the English language.

The present invention relates to a process for the preparation of 5-substituted 1-alkyltetrazolyl oxime derivatives.

5-Substituted 1-alkyltetrazolyl oxime derivatives are important intermediate compounds in active ingredient manufacture or are already fungicidally effective compounds (see e.g. WO 2010/000841). It is already known that 5-substituted 1-alkyltetrazoles can be prepared by lithiation of 1-methyltetrazole at −70° C. (cf. Can. J. Chem. 1971, 49, 2139-2142). However, the yield using the example of 5-benzoyl-1-methyltetrazole is only 41%. The 1-methyltetrazole used likewise has to be prepared in a multistage synthesis sequence. For an industrial reaction, the low temperatures and the expensive use of butyllithium are disadvantageous. Another process for the preparation of 5-benzoyl-1-methyltetrazole is known from J. Amer. Chem. Soc. 1963, 85, 2967-2976. Benzyl cyanide is reacted with ammonium azide to give 5-benzyltetrazole and then oxidized with chromium trioxide to give 5-benzoyltetrazole. The methylation to 5-benzoyl-1-methyltetrazole takes place with diazomethane. This synthesis route is likewise disadvantageous as regards safety and economical aspects. The preparation of 1-cyclohexyl-5-acetyltetrazole by reacting acetyl chloride over cyclohexyl isocyanide with subsequent reaction with hydrazoic acid is also known (cf. Chem. Ber. 1961, 94, 1116-1121). Hydrazoic acid is an unstable, extremely explosive and very toxic liquid which cannot be used on an industrial scale.

Starting from the known processes for the preparation of 5-substituted 1-alkyltetrazolyl oxime derivatives, the object now is how these can be produced safely and cost-effectively, so that the process can also be used for the industrial production of 5-substituted 1-alkyltetrazolyl oxime derivatives. A process to give 5-substituted 1-alkyltetrazolyl oxime derivatives has now been found which overcomes the aforementioned disadvantages.

The invention therefore provides a process for the preparation of 5-substituted 1-alkyltetrazolyl oxime derivatives of the general formula (I)

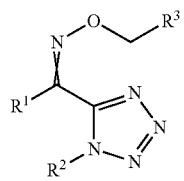

in which
$R^1$ is alkyl, or phenyl optionally monosubstituted by halogen, cyano, nitro, $C_1$-$C_8$-alkyl, $C_1$-$C_8$-alkoxy, methylsulphonyl, trifluoromethyl or aryl, $R^2$ is $C_1$-$C_{12}$-alkyl, $C_1$-$C_{12}$-haloalkyl or an alkoxyalkyl of the formula -[A-O]$_m$-B,
A is $C_2$-$C_4$-alkanediyl (alkylene),
B is $C_1$-$C_6$-alkyl,
m is 1 or 2,
$R^3$ is a pyridinyl group (Het$^1$) or a thiazolyl group (Het$^2$)

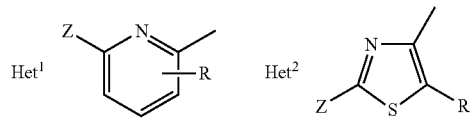

in which
R is hydrogen or halogen,
Z is hydrogen, halogen, in each case substituted or unsubstituted $C_1$-$C_8$-alkyl, $C_3$-$C_8$-cycloalkyl, $C_2$-$C_8$-alkenyl, $C_2$-$C_8$-alkynyl, or the group —N(R$^a$)C(=O)Q,
Q is hydrogen, in each case substituted or unsubstituted $C_1$-$C_8$-alkyl, $C_3$-$C_8$-cycloalkyl, $C_3$-$C_8$-cycloalkenyl-$C_1$-$C_8$-alkyl, $C_3$-$C_8$-halocycloalkyl having 1 to 5 halogen atoms, $C_3$-$C_8$-cycloalkyl-$C_1$-$C_8$-alkyl, $C_3$-$C_8$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, $C_1$-$C_8$-alkylamino, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkinyloxyimino)-$C_1$-$C_6$-alkyl, (benzyloxyimino)-$C_1$-$C_6$-alkyl, $C_1$-$C_8$-alkylsulphenyl, arylsulphenyl, tri($C_1$-$C_8$-alkyl)silyl-$C_1$-$C_8$-alkyl, tri($C_1$-$C_8$-alkyl)silyloxy, tri($C_1$-$C_8$-alkyl)silyl-$C_3$-$C_8$-cycloalkyl, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl,
$R^a$ is hydrogen, in each case substituted or unsubstituted $C_1$-$C_8$-alkyl, $C_3$-$C_8$-cycloalkyl, $C_2$-$C_8$-alkenyl, $C_2$-$C_8$-alkynyl, aryl, heterocyclyl,
characterized in that
(1) in a first step, an oximes of the general formula (II)

in which $R^1$ has the meanings given above,
is converted using a base to the salt of the oxime and is then reacted with compound of the general formula (III)

in which
$R^3$ has the meanings given above and
Y is chlorine, bromine, iodine, mesylate or tosylate,
and the oxime ethers of the general formula (IV) obtained in this way

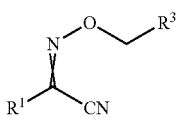

in which $R^1$ and $R^3$ have the meanings given above,
(2) are reacted in a second step with azides of the formula $R^5$—$N_3$, in which $R^5$ is sodium, potassium, tetrabutylammonium, trimethylsilyl or diphenylphosphoryl,
and the 5-substituted tetrazolyl oxime derivatives of the formula (V) obtained in this way

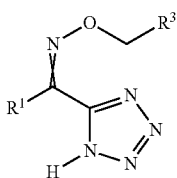

in which $R^1$ and $R^3$ have the meanings given above,
(3) are reacted in a third step with an alkylating agent of the formula (VI)

$R^2$-L     (VI)

in which
$R^2$ has the meanings given above and
L is halogen or activated hydroxy compounds.
The process according to the invention can be illustrated by the following scheme:

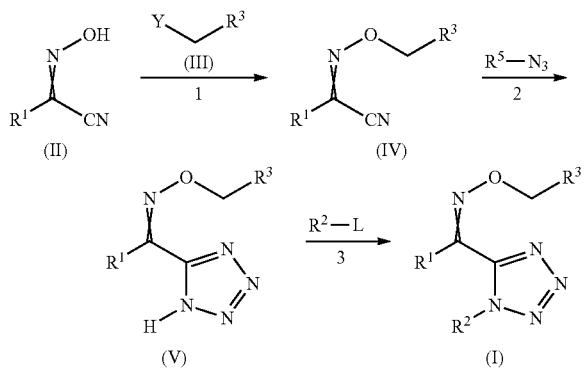

The oximes used as starting materials when carrying out the process according to the invention are generally defined by the formula (II).
$R^1$ is preferably $C_1$-$C_8$-alkyl, or phenyl optionally monosubstituted by fluorine, chlorine, bromine, iodine, cyano, nitro, $C_1$-$C_6$-alkyl, methylsulphonyl, trifluoromethyl or phenyl or naphthyl.
$R^1$ is particularly preferably $C_1$-$C_6$-alkyl, or phenyl optionally monosubstituted by fluorine, chlorine, $C_1$-$C_4$-alkyl or $C_1$-$C_3$-alkoxy.
$R^1$ is very particularly preferably methyl, ethyl, n-propyl, isopropyl, n-, s- or t-butyl, or is phenyl optionally monosubstituted by fluorine, chlorine, methyl, t-butyl, methoxy or ethoxy.
$R^1$ is especially preferably unsubstituted phenyl.

Oximes of the general formula (II) are known, e.g. commercially available, or can be prepared by known processes (cf. DE-A 28 25 565).
The compounds further used as starting materials for carrying out the process according to the invention are defined by the formula (III).
$R^3$ is preferably a pyridinyl group ($Het^1$)

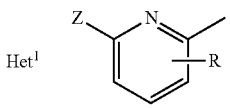

$R^3$ is also preferably a thiazolyl group ($Het^2$)

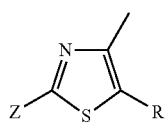

R is preferably hydrogen, fluorine, chlorine or bromine.
R is particularly preferably hydrogen.
Z is preferably hydrogen, halogen, in each case substituted or unsubstituted $C_1$-$C_6$-alkyl, $C_3$-$C_6$-cycloalkyl, $C_2$-$C_8$-alkenyl, $C_2$-$C_8$-alkynyl, or the group —N($R^a$)C(=O)Q.
Z is particularly preferably fluorine, chlorine, bromine, in each case substituted or unsubstituted $C_1$-$C_4$ alkyl, $C_2$-$C_8$-alkenyl, $C_2$-$C_8$-alkynyl, or the group —N($R^a$)C(=O)Q.
Z is very particularly preferably fluorine, chlorine, bromine, in each case substituted or unsubstituted $C_2$-$C_8$-alkenyl, $C_2$-$C_8$-alkynyl, or the group —N($R^a$)C(=O)Q.
Q is preferably hydrogen, in each case substituted or unsubstituted $C_1$-$C_6$-alkyl, $C_3$-$C_6$-cycloalkyl, $C_3$-$C_6$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl.
Q is particularly preferably in each case substituted or unsubstituted $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms.
Q is very particularly preferably $C_1$-$C_8$-alkoxy, $C_1$-$C_8$-haloalkoxy having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms.
Q is especially preferably tert-butyloxy or but-3-yn-1-yloxy.
$R^a$ is preferably hydrogen or substituted or unsubstituted $C_1$-$C_6$-alkyl.
$R^a$ is particularly preferably hydrogen.
Y is preferably chlorine, bromine, iodine, mesylate, tosylate, triflate.
Y is particularly preferably chlorine, bromine, mesylate, tosylate.

Y is very particularly preferably chlorine and bromine

The compounds of the formula (III) are known or can be prepared by known processes.

The azides further used as starting materials when carrying out the process according to the invention are generally defined by the formula $R^5$—$N_3$.

$R^5$ is preferably sodium or trimethylsilyl.

$R^5$ is particularly preferably sodium.

Azides of the formula $R^5$—$N_3$ are known, e.g. commercially available, or can be prepared by known processes.

The alkylating agents further used as starting materials when carrying out the process according to the invention are generally defined by the formula (VI).

$R^2$ is preferably $C_1$-$C_8$-alkyl, $C_1$-$C_8$-haloalkyl or an alkoxyalkyl of the formula -[A-O]$_m$-B.

$R^2$ is particularly preferably $C_1$-$C_4$-alkyl, $C_1$-$C_4$-haloalkyl or an alkoxyalkyl of the formula -[A-O]$_m$-B.

$R^2$ is very particularly preferably methyl, ethyl, trifluoromethyl, or an alkoxyalkyl of the formula -[A-O]$_m$-B.

$R^2$ is especially preferably methyl.

A is preferably —(CH$_2$)$_2$—, —(CH$_2$)$_3$—, —CH(CH$_3$)— or —CH(CH$_3$)CH$_2$—.

A is particularly preferably —(CH$_2$)$_2$— or —CH(CH$_3$)CH$_2$—.

A is very particularly preferably —(CH$_2$)$_2$—.

B is preferably $C_1$-$C_6$-alkyl.

B is particularly preferably $C_1$-$C_4$-alkyl.

B is very particularly preferably methyl or ethyl.

m is preferably 1.

L is preferably chlorine, bromine, iodine, mesylate, tosylate or SO$_2$Me.

L is particularly preferably chlorine, bromine, mesylate,

L is very particularly preferably chlorine or bromine.

The compounds of the formula (VI) are in part commercially available (such as e.g. methyl chloride, methyl bromide, methyl iodide, chlorodifluoromethane, 1-bromo-2-fluoroethane, 2-bromo-1,1-difluoroethane, 2-bromo-1-chloro-1-fluoroethane, 1-bromo-3-fluoropropane, 3-bromo-1,1-difluoroprop-1-ene) or can be obtained by known methods (cf. e.g. WO 88/00183 for 3-bromo-1,1-dichloro-prop-1-ene; cf. Houben-Weyl, Methoden der Organischen Chemie [Methods of organic chemistry], vol. V/3, Georg Thieme Verlag Stuttgart, p. 503 and vol. V/4 p. 13, 517 for compounds of the formula (VI), in which X is halogen such as chlorine, bromine and iodine; cf. *J. Org. Chem.* 1970, 35, 3195 for compounds of the formula (VI), in which Z is mesylate; *Org. Synth., Coll. Vol. I* 1941, 145 and *Org. Synth., Coll. Vol. III* 1955, 366 for compounds of the formula (VI), in which Z is tosylate).

The compounds of the formulae (I) may be present either in pure form or as mixtures of different possible isomeric forms, in particular of stereoisomers, such as E and Z, threo and erythro, and also optical isomers, such as R and S isomers or atrope isomers, but in some cases also of tautomers. Both the E and also the Z isomers, and also the threo and erythro, and also the optical isomers, any desired mixtures of these isomers, and the possible tautomeric forms are encompassed by this application. In particular, the possibility of E or Z isomers on the double bond of the oxime group may be mentioned.

In the definitions of the symbols given in the formulae above, collective terms have been used which generally representatively stand for the following substituents:

Halogen stands for fluorine, chlorine, bromine or iodine.

A heteroatom can be nitrogen, oxygen or sulphur.

Unless stated otherwise, a group or a substituted radical can be substituted by one or more of the following groups or atoms, where, in the case of multiple substitution, the substituents may be identical or different: halogen, nitro, hydroxy, cyano, amino, sulphenyl, pentafluoro-$\lambda^6$-sulphenyl, formyl, carbaldehyde-O—($C_1$-$C_8$-alkyl) oxime, formyloxy, formylamino, carbamoyl, N-hydroxycarbamoyl, formylamino, (hydroxyimino)-$C_1$-$C_6$-alkyl, $C_1$-$C_8$-alkyl, tri($C_1$-$C_8$-alkyl)silyl, tri($C_1$-$C_8$-alkyl)silyl-$C_1$-$C_8$-alkyl, $C_3$-$C_8$-cycloalkyl, tri($C_1$-$C_8$-alkyl)silyl-$C_3$-$C_8$-cycloalkyl, $C_1$-$C_8$-haloalkyl having 1 to 5 halogen atoms, $C_3$-$C_8$-halocycloalkyl having 1 to 5 halogen atoms, $C_2$-$C_8$-alkenyl, $C_3$-$C_8$-cycloalkenyl, $C_2$-$C_8$-alkynyl, $C_2$-$C_8$-alkenyloxy, $C_2$-$C_8$-alkynyloxy, $C_1$-$C_8$-alkylamino, di-$C_1$-$C_8$-alkylamino, $C_1$-$C_8$-alkoxy, $C_1$-$C_8$-haloalkoxy having 1 to 5 halogen atoms, $C_1$-$C_8$-alkylsulphenyl, $C_1$-$C_8$-haloalkylsulphenyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, $C_1$-$C_8$-alkylcarbonyl, $C_1$-$C_8$-haloalkylcarbonyl having 1 to 5 halogen atoms, $C_1$-$C_8$-alkylcarbamoyl, di-$C_1$-$C_8$-alkylcarbamoyl, N—$C_1$-$C_8$-alkyloxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-haloalkoxycarbonyl having 1 to 5 halogen atoms, $C_1$-$C_8$-alkylcarbonyloxy, $C_1$-$C_8$-haloalkylcarbonyloxy having 1 to 5 halogen atoms, $C_1$-$C_8$-alkylcarbonylamino, $C_1$-$C_8$-haloalkylcarbonylamino having 1 to 5 halogen atoms, $C_1$-$C_8$-alkoxycarbonylamino, $C_1$-$C_8$-haloalkoxycarbonylamino having 1 to 5 halogen atoms, $C_1$-$C_8$-alkylaminocarbonyloxy, di-$C_1$-$C_8$-alkylaminocarbonyloxy, $C_1$-$C_8$-alkyloxycarbonyloxy, $C_1$-$C_8$-alkylsulphenyl, $C_1$-$C_8$-haloalkylsulphenyl having 1 to 5 halogen atoms, $C_1$-$C_8$-alkylsulphynyl, $C_1$-$C_8$-haloalkylsulphinyl having 1 to 5 halogen atoms, $C_1$-$C_8$-alkylsulphonyl, $C_1$-$C_8$-haloalkylsulphonyl having 1 to 5 halogen atoms, $C_1$-$C_8$-alkylaminosulphamoyl, di-$C_1$-$C_8$-alkylaminosulphamoyl, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-haloalkoxyalkyl having 1 to 5 halogen atoms, aryl, heterocyclyl, benzyloxy, benzylsulphenyl, benzylamino, phenoxy, phenylsulphenyl or phenylamino.

Aryl is phenyl or naphthyl.

Heterocyclyl is a saturated or unsaturated 4-, 5-, 6-, 7-, 8-, 9-, 10- or 11-ring-member-containing ring having up to 4 heteroatoms.

The first reaction step (1) preferably takes place in the presence of a base. Suitable bases are organic and inorganic bases which are usually used in such reactions. Preference is given to using bases which are selected for example from the group consisting of hydrides, hydroxides, amides, alcoholates, acetates, fluorides, phosphates, carbonates and hydrogencarbonates of alkali metals or alkaline earth metals. Particular preference is given here to sodium amide, sodium hydride, lithium diisopropylamide, sodium methanolate, potassium tert-butanolate, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate and caesium carbonate. Very particular preference is given to sodium hydroxide and potassium hydroxide. Moreover, tertiary amines, such as trimethylamine, triethylamine, tributylamine, N,N-dimethylaniline, N,N-dimethylbenzylamine, pyridine, alkylpyridines, such as 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU) are preferred. Particular preference is given here to sodium methanolate, potassium tert-butanolate, caesium carbonate, sodium hydride.

The molar ratio of base to the compound of the formula (II) used is for example 0.8-10, preferably 0.9-6, particularly preferably 1.0-3. The use of larger amounts of base is possible in principle, but does not lead to any preferred embodiment and is disadvantageous for reasons of cost.

It is also possible to firstly prepare and isolate the salt of the oxime ether (II) and then use it in step (1). The oxime ethers of the formula (IV) obtained in step (1) can either be isolated or be further reacted directly in situ.

The ratio of the oxime of the formula (II) used to the compound of the formula (III) used can vary. Preferably, the ratio of the oxime of the formula (II) to the compound of the formula (III) used is in the range from 0.6:1 to 1:2, in particular in the range from 0.8:1 to 1:1.5, specifically from 0.9:1.1 to 1:1.4.

In step (1), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents are also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons (e.g. pentane, hexane, heptane, octane, nonane, such as the so-called "white spirits" with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene); halogenated hydrocarbons, such as chlorobenzene, dichlorobenzene, dichloromethane, chloroform, tetrachloromethane, dichloroethane or trichloroethane; esters (e.g. methyl, ethyl, butyl, isobutyl acetate, dimethyl, dibutyl or ethylene carbonate, propylene carbonate); amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylprrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; ketones such as acetone or mixtures thereof.

For the reaction according to the invention, the solvents used are preferably aromatic and/or aliphatic hydrocarbons, amides, nitriles, ethers, in particular DMF, N,N-dimethylacetamide, toluene, acetonitrile, THF, methylene chloride or mixtures of these solvents.

The process according to the invention can generally be carried out in vacuo, at atmospheric pressure or superatmospheric pressure.

The process according to the invention in step (1) takes place at temperatures of from −20 to +150° C., preferably at temperatures of from −10 to +100° C.

Step (2) of the process according to the invention is optionally carried out in the presence of an auxiliary. Auxiliaries which can be used are ammonium azides (Houben-Weyl; volume E8d, Hetarenes III/part 4; 1994; pages 677-720), guanidinium salts or aluminium salts. These ammonium azides can be prepared easily in situ by mixing sodium azide and ammonium chloride. Further catalysts are zinc salts such as e.g. $ZnCl_2$, $ZnBr_2$, $Zn(ClO_4)_2$ or ionic liquids such as 1-butyl-3-methylimidazolium, 1-methyl-3-methylimidazolium, 1-hexyl-3-methylimidazolium, 1-octyl-3-methylimidazolium.

The molar ratio of auxiliary to the compound of the formula (IV) used is for example 0.8-10, preferably 0.9-6, particularly preferably 1.0-3. The use of larger amounts of auxiliary is possible in principle, but does not lead to any preferred embodiment and is disadvantageous for reasons of cost.

The ratio of oxime ether of the formula (V) to the azide of the formula $R^5$—$N_3$ can vary. A significant excess is not critical for the reaction, but is uneconomic. Preferably, the ratio of oxime ether of the formula (IV) to the azide of the formula $R^5$—$N_3$ is in the range from 1:1 to 1:3, in particular in the range from 1:1 to 1:2, specifically in the range from 1:1.0 to 1:1.3.

In step (2), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents are also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; or mixtures thereof.

For the reaction according to the invention, the solvents preferably used are amides, nitriles, ethers, in particular acetonitrile, THF, DMF, or mixtures thereof.

The process according to the invention can generally be carried out in vacuo, at atmospheric pressure or at superatmospheric pressure.

The process according to the invention in step (2) takes place at temperatures of from 0 to +170° C., preferably at temperatures of from 10 to +150° C.

The third reaction step (3) preferably takes place in the presence of a base. Suitable bases are organic and inorganic bases which are usually used in such reactions. Preference is given to using bases which are selected for example from the group consisting of hydrides, hydroxides, amides, alcoholates, acetates, phosphates, carbonates and hydrogencarbonates of alkali metals or alkaline earth metals. Particular preference is given here to sodium amide, sodium hydride, lithium diisopropylamide, sodium methanolate, potassium tertbutanolate, sodium hydroxide, potassium hydroxide, sodium acetate, sodium phosphate, potassium phosphate, sodium carbonate, potassium carbonate, potassium hydrogencarbonate, sodium hydrogencarbonate and caesium carbonate. Very particular preference is given to carbonates such as e.g. sodium carbonate, caesium carbonate, potassium carbonate. Moreover, tertiary amines, such as trimethylamine, triethylamine, tributylamine, N,N-dimethylaniline, N,N-dimethylbenzylamine, pyridine, alkylpyridines, such as 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU) are preferred. Particular preference is given here to sodium methanolate, potassium tert-butanolate, caesium carbonate, sodium hydride.

The molar ratio of base to the compound of the formula (IV) used is for example 0.8-10, preferably 0.9-6, particularly preferably 1.0-3. The use of larger amounts of base is possible in principle, but does not lead to a preferred embodiment and is disadvantageous for reasons of cost.

The ratio of the tetrazole of the formula (V) used to the compound of the formula (VI) used can vary. Preferably, the ratio of tetrazole of the formula (V) to the compound of the formula (VI) used is in the range from 0.6:1 to 1:2, in particular in the range from 0.8:1 to 1:1.5, specifically from 0.9:1.1 to 1:1.4.

In step (3), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents are also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons (e.g. pentane, hexane, heptane, octane, nonane, such as the so-called "white spirits" with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene); halogenated hydrocarbons, such as chlorobenzene, dichlorobenzene, dichloromethane, chloroform, tetrachloromethane, dichloroethane or trichloroethane; esters (e.g. methyl, ethyl, butyl, isobutyl acetate, dimethyl, dibutyl or ethylene carbonate, propylene carbonate); amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; ketones such as acetone or mixtures thereof.

For the reaction according to the invention, the solvents used are preferably aromatic and/or aliphatic hydrocarbons, amides, nitriles, ethers, in particular DMF, N,N-dimethylacetamide, toluene, acetonitrile, THF, methylene chloride or mixtures of these solvents.

The process according to the invention can generally be carried out in vacuo, at atmospheric pressure or superatmospheric pressure.

The process according to the invention in step (3) takes place at temperatures of from −20 to +120° C., preferably at temperatures of from −10 to +100° C.

The present invention is illustrated in more detail by reference to the examples below, without thereby limiting the invention thereto.

PREPARATION EXAMPLES

Example 1

But-3-yn-1-yl{6-[({[(Z)-cyano(phenyl)methylene]amino}oxy)methyl]pyridin-2-yl}carbamate

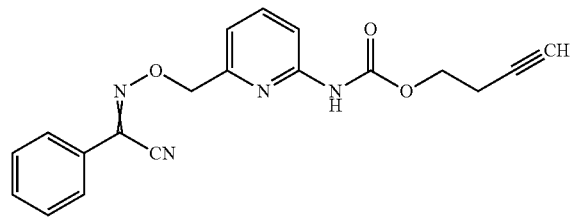 [SMILES: C#CCCOC(=O)Nc1cccc(CON=C(C#N)c2ccccc2)n1]

Phenylacetonitrile (9.72 g, 82.97 mmol) was metered into a suspension of 3.31 g (82.97 mmol) of NaOH in 60 ml of ethanol. Following the complete addition, 11.66 g (99.56 mmol) of isopentyl nitrite were metered in dropwise at temperatures of 15° C. The mixture was then stirred for a further 2 hours at this temperature. The reaction mixture was diluted with 300 ml of diethyl ether, and the precipitated solid was filtered off and washed twice with in each case 50 ml of diethyl ether. The white salt sodium {[(Z)-cyano(phenyl)methylene]amino}oxidanide (7.89 g, 56% yield) can be dried in vacuo or be further used directly. 1.49 g (6.24 mmol) of but-3-yn-1-yl[6-(chloromethyl)pyridin-2-yl]carbamate and 103 mg (0.624 mmol) of potassium iodide were added to a solution of 1.05 g (6.24 mmol) of sodium {[(Z)-cyano(phenyl)methylene]amino}oxidanide in 25 ml of acetonitrile and 10 ml of DMF. The reaction mixture was stirred for 7 h at room temperature, the solvent was removed in vacuo and the residue was dissolved in 100 ml of ethyl acetate. The organic phase was washed with water and dried over MgSO$_4$. After removing the solvent, 2.21 g (99% yield, only 1 oxime isomer) of but-3-yn-1-yl{6-[({[(Z)-cyano(phenyl)methylene]-amino}oxy)methyl]pyridin-2-yl}carbamate were isolated as a colourless solid.

$^1$H-NMR (250 MHz, DMSO-d$_6$/DMSO-d$_5$=2.50, water signal at=3.33): δ (ppm)=10.37 (s, 1H), 7-85-7.79 (m, 2H), 7.76-7.72 (m, 2H), 7.60-7.55 (m, 3H), 7.20-7.15 (dd, J=6.0 and 2.2 Hz, 1H), 5.44 (s, 2H), 4.18 (t, J=6.7 Hz, 2H), 2.91 (t, J=2.6 Hz, 1H), 2.54 (td, J=6.7 and 2.6 Hz, 2H).

Example 2

But-3-yn-1-yl{6-[({[(Z)-phenyl(1H-tetrazol-5-yl)methylene]amino}oxy)methyl]pyridin-2-yl}carbamate

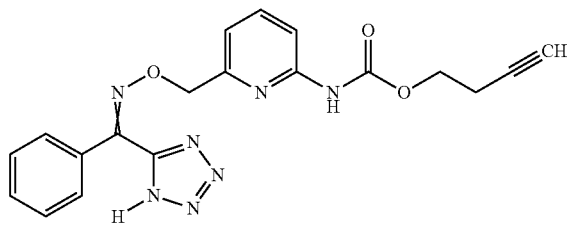 [SMILES: C#CCCOC(=O)Nc1cccc(CON=C(c2ccccc2)c2nnn[nH]2)n1]

A solution of 442 mg (1.269 mmol) of but-3-yn-1-yl {6-[({[(Z)-cyano(phenyemethylene]amino}oxy)-methyl]pyridin-2-yl}carbamate in 4 ml of DMF was heated to 60° C. Then, 348 mg (2.53 mmol) of triethylamine hydrochloride and 164 mg (2.53 mmol) of sodium azide were added in equal portions over 12 h at 60° C. The reaction mixture was cooled to room temperature and admixed with 20 ml of water. The mixture was extracted three times with 20 ml ethyl acetate. The combined organic phases were dried over MgSO$_4$. After removing the solvent, 463 mg (92% yield) of but-3-yn-1-yl {6-[({[(Z)-phenyl(1H-tetrazol-5-yl)methylene]amino}oxy)methyl]pyridin-2-yl}carbamate were obtained as a colourless solid. The product comprises 4% of the (E)-isomer. Recrystallization form heptane/ethyl acetate gave 99% pure (Z)-isomer.

$^1$H-NMR (500 MHz, DMSO-d$_6$/DMSO-d$_5$=2.50, water signal at=3.33): δ (ppm)=10.27 (s, 1H), 7.82-7.75 (m, 2H), 7.53-7.44 (m, 5H), 7.09 (d, J=6.9 Hz, 1H), 5.32 (s, 2H), 4.18 (t, J=6.6 Hz, 2H), 3.6-3.2 (bs, 1H), 2.91 (t, J=2.6 Hz, 1H), 2.54 (td, J=6.7 and 2.6 Hz, 2H).

Example 3

But-3-yn-1-yl{6-[({[(Z)-(1-methyl-1H-tetrazol-5-yl)(phenyl)methylene]amino}oxy)methyl]-pyridin-2-yl}carbamate

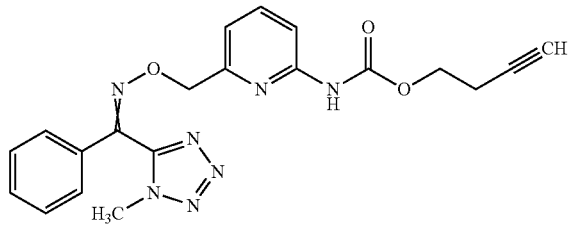 [SMILES: C#CCCOC(=O)Nc1cccc(CON=C(c2ccccc2)c2nnnn2C)n1]

19.9 mg (0.061 mmol) of caesium carbonate and a solution of methyl chloride in MTBE (1 N, 0.128 ml, 0.128 mmol, 2.5 eq.) were added to a solution of 20 mg (0.051 mmol) of but-3-yn-1-yl{6-[{[(Z)-phenyl(1H-tetrazol-5-yl)methylene]amino}oxy)methyl]pyridin-2-yl}carbamate in 1 ml of acetonitrile. The reaction mixture was stirred for 5 h at 60° C. The solvent was removed in vacuo and the residue was dissolved in EtOAc. After adding water, the phases were separated and the aqueous phase was extracted twice with 10 ml of EtOAc. The combined organic phases were dried over MgSO$_4$. After removing the solvent, a mixture of 62% but-3-yn-1-yl {6-[({[(Z)-(1-methyl-1H-tetrazol-5-yl)(phenyl)methylene]amino}oxy)methyl]pyridin-2-yl}carbamate and 38% of but-3-yn-1-yl{6-[({[(Z)-(2-methyl-2H-tetrazol-5-yl)(phenyl)methylene]amino}oxy)methyl]pyridin-2-yl}carbamate (23 mg, 96%, 87% purity) were obtained as an oil.

$^1$H-NMR (400 MHz, DMSO-d$_6$/DMSO-d$_5$=2.50, water signal at=3.33): δ (ppm)=10.30 (s, 1H), 7.84-7.76 (m, 2H), 7.58-7.40 (m, 5H), 7.08-7.02 (m, 1H), 5.29 (s, 2H), 4.18 (t, J=6.7 Hz, 2H), 4.05 (s, 3H), 2.91 (t, J=2.7 Hz, 1H), 2.56 (td, J=6.5 and 2.6 Hz, 2H).

The invention claimed is:
1. A process for the preparation of 5-substituted 1-alkyltetrazolyl oxime derivatives of the general formula (I)

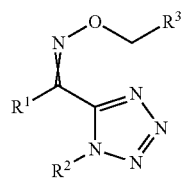

in which
R$^1$ is alkyl, or phenyl optionally monosubstituted by halogen, cyano, nitro, C$_1$-C$_8$-alkyl, C$_1$-C$_8$-alkoxy, methylsulphonyl, trifluoromethyl or aryl,
R$^2$ is C$_1$-C$_{12}$-alkyl, C$_1$-C$_{12}$-haloalkyl or an alkoxyalkyl of the formula -[A-O]$_m$-B,
A is C$_2$-C$_4$-alkanediyl (alkylene),
B is C$_1$-C$_6$-alkyl,
m is 1 or 2,
R$^3$ is a pyridinyl group (Het$^1$) or a thiazolyl group (Het$^2$)

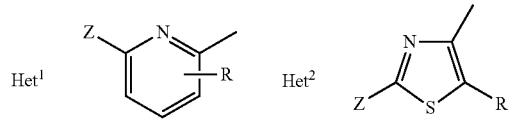

in which
R is hydrogen or halogen,
Z is hydrogen, halogen, in each case substituted or unsubstituted C$_1$-C$_8$-alkyl, C$_3$-C$_8$-cycloalkyl, C$_2$-C$_8$-alkenyl, C$_2$-C$_8$-alkynyl, or the group —N(R$^a$)C(=O)Q,
Q is hydrogen, in each case substituted or unsubstituted C$_1$-C$_8$-alkyl, C$_3$-C$_8$-cycloalkyl, C$_3$-C$_8$-cycloalkenyl-C$_1$-C$_8$-alkyl, C$_3$-C$_8$-halocycloalkyl having 1 to 5 halogen atoms, C$_3$-C$_8$-cycloalkyl-C$_1$-C$_8$-alkyl, C$_3$-C$_8$-cycloalkenyl, C$_2$-C$_8$-alkenyl, C$_2$-C$_8$-haloalkenyl having 1 to 5 halogen atoms, C$_2$-C$_8$-alkynyl, C$_2$-C$_8$-haloalkynyl having 1 to 5 halogen atoms, C$_1$-C$_8$alkoxy, C$_1$-C$_8$-haloalkoxy having 1 to 5 halogen atoms, C$_1$-C$_8$-haloalkoxyalkyl having 1 to 5 halogen atoms, C$_2$-C$_8$-alkenyloxy, C$_2$-C$_8$-haloalkenyloxy having 1 to 5 halogen atoms, C$_3$-C$_8$-alkynyloxy, C$_3$-C$_8$-haloalkynyloxy having 1 to 5 halogen atoms, $C_1$-$C_8$-alkylamino, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkinyloxyimino)-$C_1$-$C_6$-alkyl, (benzyloxyimino)-$C_1$-$C_6$-alkyl, $C_1$-$C_8$-alkylsulphenyl, arylsulphenyl, tri-($C_1$-$C_8$-alkyl)silyl-$C_1$-$C_8$-alkyl, tri($C_1$-$C_8$-alkyl)silyloxy, tri($C_1$-$C_8$-alkyl)silyl-$C_3$-$C_8$-cycloalkyl, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl, $R^a$ is hydrogen, in each case substituted or unsubstituted $C_1$-$C_8$-alkyl, $C_3$-$C_8$-cycloalkyl, $C_2$-$C_8$-alkenyl, $C_2$-$C_8$-alkynyl, aryl, heterocyclyl, the process comprising the steps of:

(1) in a first step, converting an oxime of the general formula (II)

(II)

in which $R^1$ has the meanings given above, by using a base, to the salt of the oxime, which is then reacted with a compound of the general formula (III)

(III)

$Y\diagdown R^3$ in which $R^3$ has the meanings given above and

Y is chlorine, bromine, iodine, mesylate or tosylate, (2) in a second step, reacting oxime ethers of the general formula (IV) obtained in the first step (IV)

in which $R^1$ and $R^3$ have the meanings given above, with an azide of the formula $R^5$—$N_3$, in which $R^5$ is sodium, potassium, tetrabutylammonium, trimethylsilyl or diphenylphosphoryl, and in a third step, reacting 5-substituted tetrazolyl oxime derivatives of the formula (V) obtained in the second step (V)

in which $R^1$ and $R^3$ have the meanings given above, with an alkylating agent of the formula (VI)

$$R^2\text{-L} \qquad (VI)$$

in which $R^2$ has the meanings given above and

L is halogen or an activated hydroxy compound.

2. The process according to claim 1, wherein oximes of the formula (II), compounds of the formula (III) and alkylating agents of the formula (VI) are used in which $R^1$ is $C_1$-$C_8$-alkyl, or phenyl optionally monosubstituted by fluorine, chlorine, bromine, iodine, cyano, nitro, $C_1$-$C_6$-alkyl, methylsulphonyl, trifluoromethyl or phenyl or naphthyl, $R^2$ is $C_1$-$C_8$-alkyl, $C_1$-$C_8$-haloalkyl or an alkoxyalkyl of the formula -[A-O]$_m$-B, A is —($CH_2$)$_2$—, —($CH_2$)$_3$—, —CH($CH_3$)— or —CH($CH_3$)$CH_2$—, B is $C_1$-$C_6$-alkyl, m is 1, $R^3$ is a pyridinyl group (Het$^1$) or a thiazolyl group (Het$^2$)

in which

R is hydrogen, fluorine, chlorine or bromine,

Z is hydrogen, halogen, in each case substituted or unsubstituted $C_1$-$C_6$-alkyl, $C_3$-$C_6$-cycloalkyl, $C_2$-$C_8$-alkenyl, $C_2$-$C_8$-alkynyl, or the group —N($R^a$)C(=O)Q, Q is hydrogen, in each case substituted or unsubstituted $C_1$-$C_6$-alkyl, $C_3$-$C_6$-cycloalkyl, $C_3$-$C_6$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl, $R^a$ is hydrogen or substituted or unsubstituted $C_1$-$C_6$-alkyl, Y is chlorine, bromine, iodine, mesylate, tosylate, or triflate.

3. The process according to claim 1, wherein step (1) is carried out in the presence of a base.

4. The process according to claim 3, wherein the molar ratio of base to the oxime of the formula (II) used is 0.8-10.

5. The process according to claim 1, wherein step (1) is carried out in a solvent.

6. The process according claim 5, wherein step (2) is carried out in the presence of a base.

7. The process according to claim 6, wherein the molar ratio of base to the compound of the formula (IV) used is 0.8-10.

* * * * *